US008628539B2

(12) United States Patent
Edelman et al.

(10) Patent No.: US 8,628,539 B2
(45) Date of Patent: Jan. 14, 2014

(54) FLEXIBLE DISPOSABLE SURGICAL PORT

(75) Inventors: David S. Edelman, Miami, FL (US); Leonard Pinchuk, Miami, FL (US)

(73) Assignee: Innovia, LLC, Miami, FL (US)

( * ) Notice: Subject to any disclaimer, the term of this patent is extended or adjusted under 35 U.S.C. 154(b) by 1196 days.

(21) Appl. No.: 12/468,219

(22) Filed: May 19, 2009

(65) Prior Publication Data

US 2010/0063452 A1 Mar. 11, 2010

Related U.S. Application Data

(60) Provisional application No. 61/094,706, filed on Sep. 5, 2008.

(51) Int. Cl.
*A61M 39/02* (2006.01)

(52) U.S. Cl.
USPC .......................................... 606/108; 600/114

(58) Field of Classification Search
USPC ............ 606/108; 604/174, 539; 600/114, 115
See application file for complete search history.

(56) References Cited

U.S. PATENT DOCUMENTS 5,176,649 A 1/1993 Wakabayashi
5,342,316 A 8/1994 Wallace
5,514,133 A 5/1996 Golub et al.
5,545,179 A * 8/1996 Williamson, IV ............ 604/256
5,628,732 A 5/1997 Antoon, Jr. et al.
5,830,191 A 11/1998 Hildwein et al.
6,099,506 A 8/2000 Macoviak et al.
6,383,191 B1 5/2002 Zdeblick et al.
6,454,783 B1 9/2002 Piskun
6,551,270 B1 * 4/2003 Bimbo et al. .............. 604/93.01
7,316,699 B2 1/2008 McFarlane
7,344,547 B2 3/2008 Piskun
2003/0171713 A1 9/2003 McFarlane
2005/0004592 A1 1/2005 Criscuolo
2005/0137609 A1 * 6/2005 Guiraudon .................... 606/108
2006/0020241 A1 1/2006 Piskun et al.
2006/0270911 A1 * 11/2006 Voegele et al. ............... 600/235
2007/0225650 A1 9/2007 Hart et al.
2008/0027476 A1 1/2008 Piskun
2008/0255519 A1 * 10/2008 Piskun et al. ................. 604/174
2008/0306580 A1 * 12/2008 Jenson et al. ................ 606/159

OTHER PUBLICATIONS

Triport Brochure, Access the Future of Laparoscopic Surgery, Advanced Concepts, 2000 (1 page).
Uni-X™ System, UNI-X Single Port Laparoscopy, available at http://www.pnavel.com/patient.html, 2008 (1 page).

* cited by examiner

*Primary Examiner* — Thomas McEvoy
*Assistant Examiner* — Sarah W Aleman
(74) *Attorney, Agent, or Firm* — Gordon & Jacobson, PC

(57) ABSTRACT

A surgical apparatus for introduction of laparoscopic instruments into an anatomical cavity through tissue at an entry site. The apparatus includes a body with a frustoconical-shaped wall. The body defines an interior cavity, an open bottom, and a substantially closed top wall with openings from which a plurality of ports extend upward therefrom. The ports are adapted to receive the laparoscopic instruments for introduction through the interior cavity and open bottom of the body into the anatomical cavity. In the preferred embodiment, the frustoconical-shaped wall of the body is placed through an incision in the umbilicus. In one aspect of the invention, the body is a unitary one-piece molded structure. A reinforcing belt or plate formed from a relatively hard material can be integral to the body. In another aspect, the apparatus is formed from a block copolymer of poly(styrene-block-isobutylene-block-styrene), hereinafter referred to as "SIBS", which unexpectedly provides the benefit that lubrication of the ports (or of the instruments extending through the ports) is avoided.

18 Claims, 7 Drawing Sheets

441 480 413 413 400 411 480 482 442 481 482 426 422 442

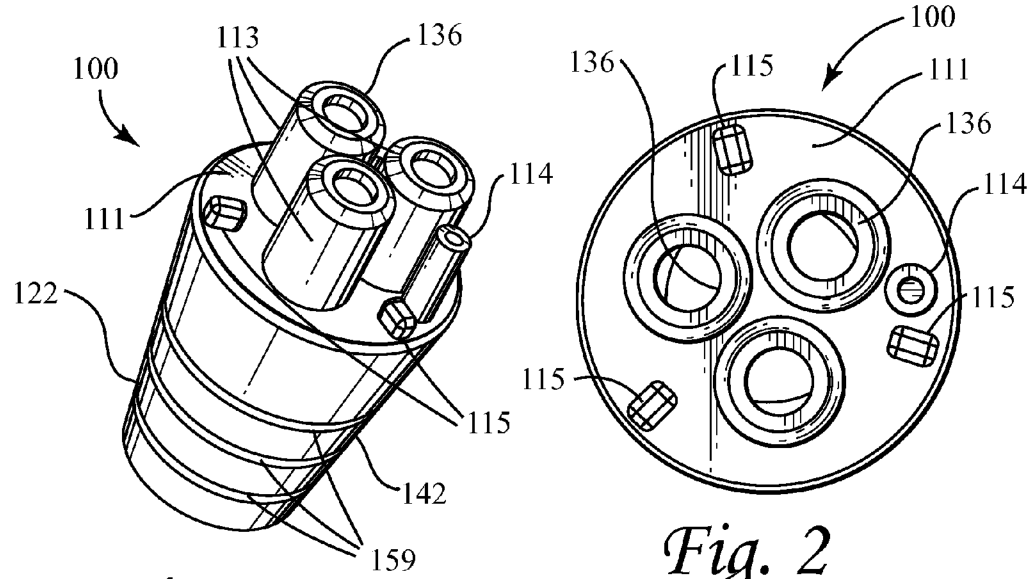
Fig. 1
Fig. 2
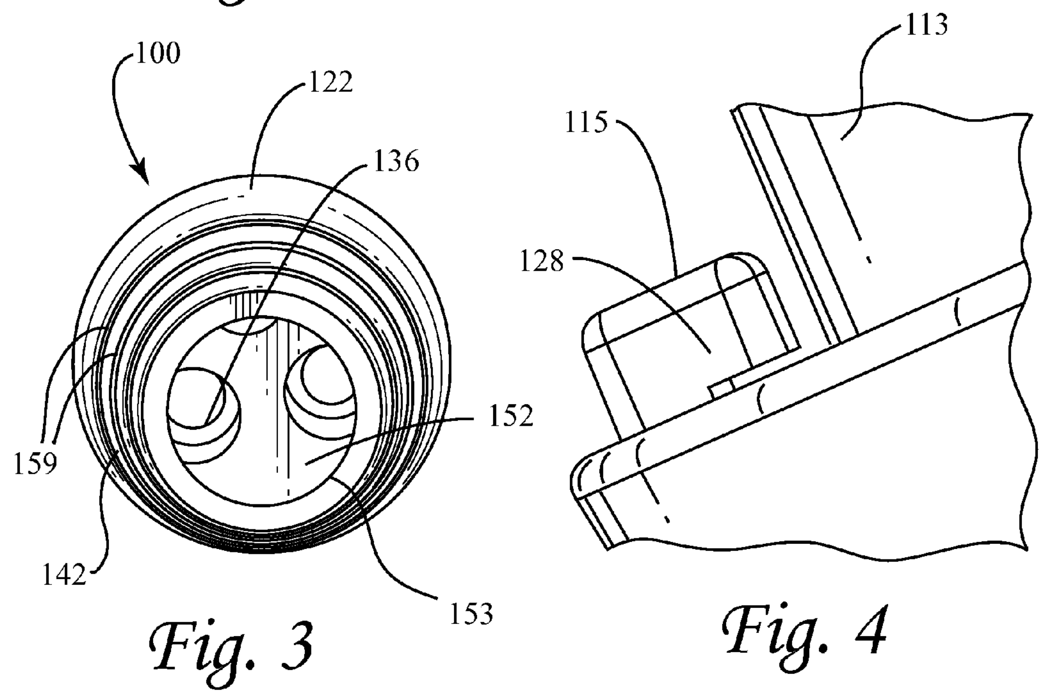
Fig. 3
Fig. 4

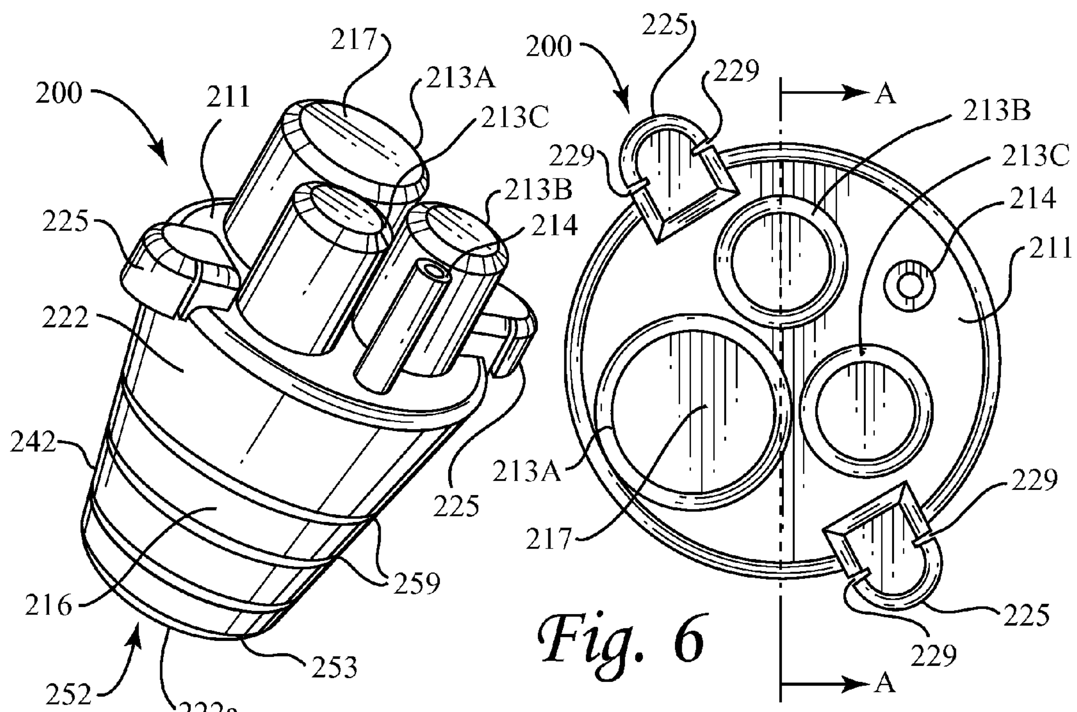
Fig. 5
Fig. 6
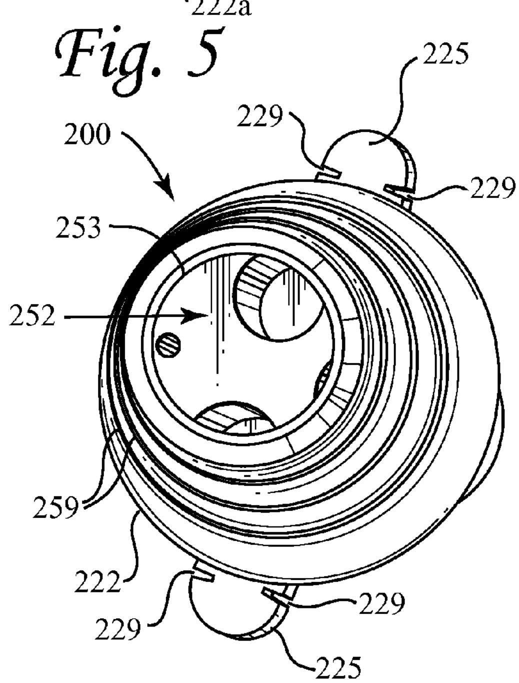
Fig. 7
213B
213A
200
225
242
242
α
252
222a
216
Fig. 8

FLEXIBLE DISPOSABLE SURGICAL PORT

CROSS-REFERENCE TO RELATED APPLICATIONS

This application claims benefits from U.S. Provisional Patent Application No. 61/094,706, filed Sep. 5, 2008, the contents of which are hereby incorporated herein by reference.

BACKGROUND OF THE INVENTION

1. Field of the Invention

The invention broadly relates to surgical ports. The invention more particularly relates to surgical ports for abdominal surgery, although it is not limited thereto.

2. State of the Art

Endoscopic or laparoscopic surgery has existed for over two decades. The surgery usually involves making three small incisions in the abdomen, into which endoscopic surgical tools such as scissors, graspers etc., are introduced through trocar sleeves. Surgical trocars generally include a cylinder with a sharply pointed end and a sleeve around the cylinder. The pointed end of the cylinder is used to make a hole in the abdomen and facilitates entry of the sleeve into the body cavity. When the cylinder is removed from the sleeve, the sleeve provides a port through which instrumentation may be introduced.

Instrumentation for laparoscopic surgery may include an insufflation means (usually a carbon dioxide source and tubing), a fiber optic light, a forceps (grasper), a scissors, a stapler, a clip applier, a video camera, etc., depending upon the nature of the surgery. The proximal end of the trocar may include one or more valves such as flapper valves or washer valves which are attached to the cylinder for preventing escape of gas (desufflation) from the abdominal cavity as the instrumentation is placed into and removed from the trocar sleeve.

SUMMARY OF THE INVENTION

The present invention provides a flexible surgical port device which can be placed through an incision in the belly button (umbilicus). The device of the invention incorporates three or more ports in the device so that laparoscopic surgery requiring three ports can be conducted through the device without the necessity of making additional incisions in the abdomen.

According to an aspect of the invention, a molded flexible elastic disposable port includes a hollow generally frustoconical body having an open bottom and a generally closed top defining at least three and preferably four port holes, and at least three and preferably four ports integral with the body, including three ports with valves for receiving surgical instruments, and one for receiving an insufflation source extending upwards from the top which are in fluid communication with the port holes. In use, a plurality of endoscopic instruments are passed through the ports and through the central cavity defined by the frustoconical body into the abdominal cavity to allow for manipulation of the instruments inside the abdominal cavity.

According to one aspect of the invention, the flexible disposable port is a single piece which is molded from an elastic material, and valves are formed in the elastic material.

According to another aspect of the invention, the flexible disposable port is an insert molded piece formed of an elastic molded material and having a belt or plate formed from a relatively hard material inserted therein, where the valves are formed in the molded elastic material.

According to a further aspect of the invention, the flexible disposable port including the port valves is molded from a block copolymer of poly(styrene-block-isobutylene-block-styrene), hereinafter referred to as "SIBS", which unexpectedly provides the benefit that lubrication of the valves or of the instruments extending through the valves is not needed.

It will be appreciated that the umbilicus is a unique structure as a large incision can actually be hidden in it as it is already just a big scar. In addition, it stretches more than most tissue. For example, one can make a 15 mm incision in the umbilicus and stretch the opening to approximately 30 mm. The fascia underneath the umbilicus may be more tense than the umbilicus tissue. However, the fascia can be cut to allow a larger opening without concern of a visible cosmetic scar.

Objects and advantages of the invention will become apparent to those skilled in the art upon reference to the detailed description taken in conjunction with the provided figures.

BRIEF DESCRIPTION OF THE DRAWINGS

FIG. 1 is perspective view of a first embodiment of a flexible port device in accordance with the present invention.

FIG. 2 is a top view of the device of FIG. 1.

FIG. 3 is a bottom view of the device of FIG. 1.

FIG. 4 is an enlarged view of the suture catch of the device of FIG. 1.

FIG. 5 is a perspective view of a second embodiment of a flexible port device in accordance with the present invention.

FIG. 6 is a top view of the device of FIG. 5.

FIG. 7 is a bottom view of the device of FIG. 5.

FIG. 8 is a sectional view through the device of FIG. 5 along line 8-8 of FIG. 6.

DETAILED DESCRIPTION OF THE PREFERRED EMBODIMENTS

Figure 9:
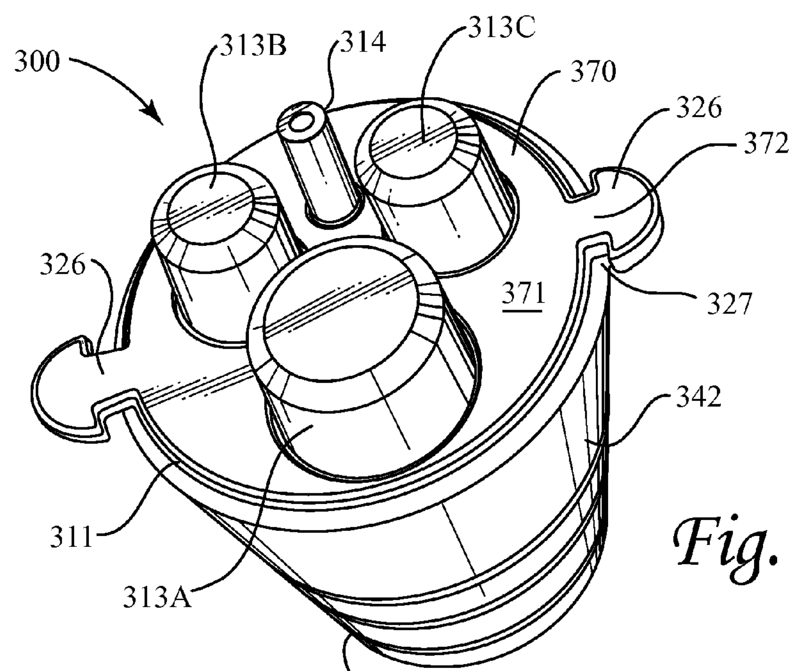
FIG. 9 is a perspective view of a third embodiment of a flexible port device in accordance with the present invention.

A first embodiment of a flexible disposable port 100 in accordance with the present invention is shown in FIGS. 1-4. The port 100 is formed of a single molded piece of flexible material and includes a flexible top wall 111 having three working ports 113, an insufflation port 114 (for insufflation/desufflation) and suture retention means 115 integral there-with and extending outwardly therefrom, and a hollow frustoconical body 122 which is open at the bottom and is closed by the flexible top wall 111.

The working ports 113 each have an inner diameter of approximately 7 mm, although ports of different diameters can be utilized. As will be discussed hereinafter, the working ports are provided with seals or valves which are designed to seal about nominally 5 mm laparoscopic tools. The inner diameter of the insufflation port 114 is approximately 3-5 mm, and insufflation port 114 is adapted to receive a tube (not shown) which is coupled to a source of gas/suction.

As seen best in FIG. 2, three suture retention means 115 are provided and are spaced at one hundred twenty degree intervals, although a different number of suture retention means may be utilized and/or different spacings could be used. As seen in FIG. 4, each of the suture retention means 115 defines a slot 128 at its base. The slot is provided such that a suture may be snagged in the slot between the top wall 111 and the suture retention means 115.

Each of the working ports 113 can be fitted with a valve to prevent pressure loss when an instrument is removed from the port. In the illustrated embodiment, the entrance to the working ports 113 are fitted with a flexible O-shaped seal 136, which is preferably realized as a thin stretchable membrane having an open circular hole (approximately 4 mm in diameter) in its center as shown in FIGS. 1-3. The O-seal 136 is preferably molded as part of the port 100 and configured to seal against an instrument passing therethrough during use. The O-seal 136 may be used in conjunction with a flapper valve (not shown) as is known in the trocar arts. Alternatively, if desired, the valve may be formed as part of the molded port 100 by causing the top of each port 113 to be closed, and then by slitting the top to generate a slit valve (e.g., an X, Y, I or arcuate slit). As another alternative, a tricuspid valve or a duck-bill valve may be formed as part of the mold or may be separately provided and fit to the ports as is well known in the industry. In yet another alternative embodiment, little plugs which can fit into the ports 113 and having associated arms (not shown) attached to top wall 111 can be molded as part of the port 100 and can be used to close ports 113 when tools are not extending through the ports 113.

As shown in FIG. 3, the hollow frustoconical body 122 extends distally from the perimeter of the top wall 111 and is configured for insertion into a single incision in the umbilicus. The frustoconical body 122 has a tapered sidewall 142 which defines a central cavity 152 with an opening 153 opposite the top wall 111. In the shown embodiment, the tapered sidewall 142 includes circumferential grooves or dents 159 which are spaced apart along the exterior surface of the tapered sidewall 142. The grooves 159 can assist a surgeon in cutting or otherwise trimming the tapered sidewall 142 to a desired length with a scissors or sharp scalpel if so desired.

FIGS. 5-9 show an alternate embodiment of a port device 200. In the alternate embodiment of FIGS. 5-9, like numerals (increased by 100) are used to refer to the structural elements that are similar to those of the embodiment described above with respect to FIGS. 1-4. In this embodiment, the working ports 213 of port 200 have different diameters. For example, as shown, the working port 213A is larger in diameter than the working ports 213B and 213C. In the preferred embodiment, port 213A is approximately 12 mm in diameter to accept a 10 mm diameter stapler, clip applier, or other nominally 10 mm tools, while ports 213B and 213C are 7 mm in diameter for smaller (5 mm diameter) instruments such as scissors and graspers. Each of the working ports 213A, 213B, 213C is shown molded with a membrane 217 which can be slit to form a slit valve (e.g., an X or Y slit) or may be left as a blank and punctured by instrumentation at the time of use. Alternatively, each port may be molded with a tricuspid or duck-bill valve, or the O-shaped seal having an open circular hole in its center as shown in the first embodiment. As another alternative, each port may be fitted with a valve (not shown) to prevent pressure loss (desufflation) when an instrument is removed from the port.

The port 200 also preferably includes a plurality of suture retention means 225 (for example, two shown) disposed about the periphery of the top wall 211. The suture retention means 225 comprises a tab or ear that extends radially outward beyond the perimeter of the top wall 211 (preferably in or substantially parallel to the plane of the top wall as shown). The tab defines slots 229 that preferably extend parallel to the central axis 216 of the port 200. The slots 229 are disposed radially outward from the perimeter of the top wall 211 and tapered sidewall 222 of body as best shown in FIGS. 6 and 7. The slots 229 are adapted to grab or otherwise hold sutures inserted therein for fixation of the port 200 during use.

Figure 10:
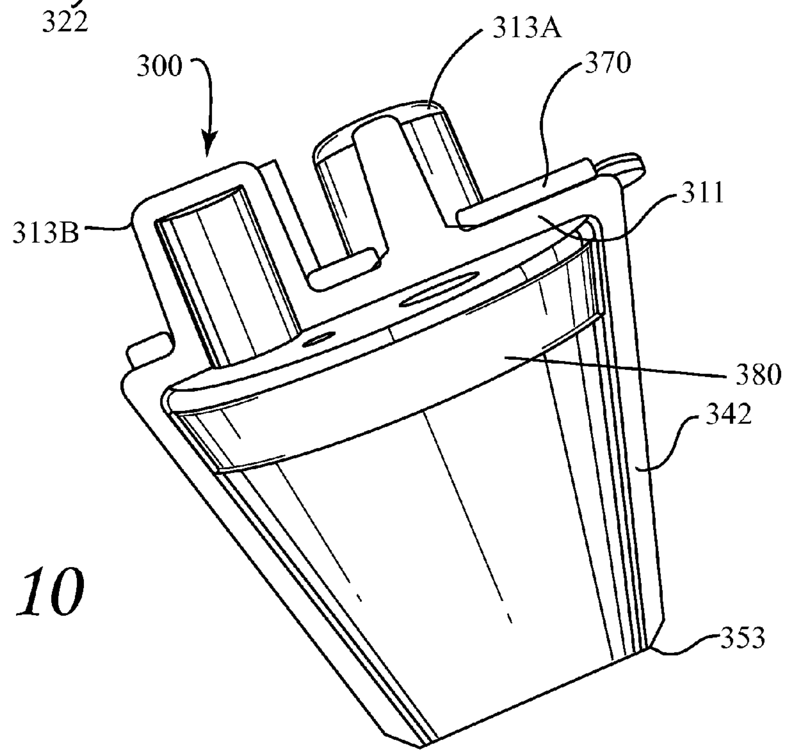
FIG. 10 is sectional view of the device of FIG. 9.
Figure 11:
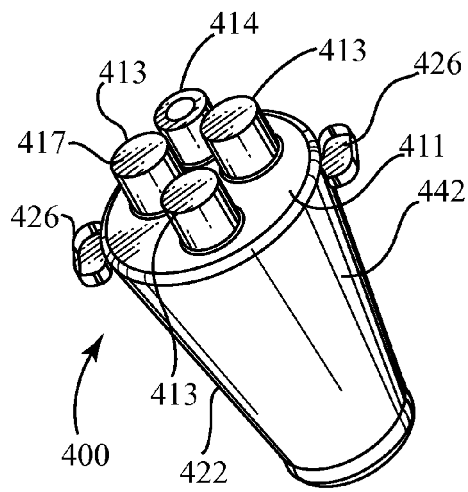
FIG. 11 is a perspective view of a fourth embodiment of a flexible port device in accordance with the present invention.
Figure 13:
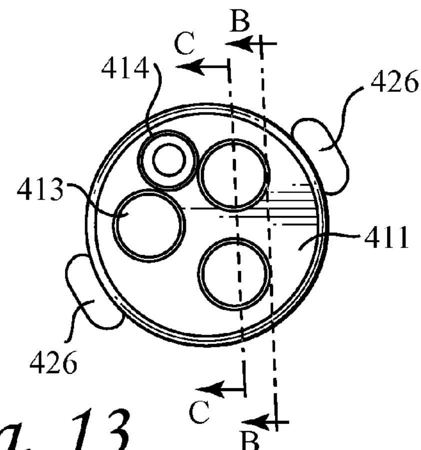
FIG. 13 is a top view of the device of FIG. 11.

FIGS. 9 and 10 show an alternate embodiment of a port device 300. In the alternate embodiment of FIGS. 9 and 10, like numerals (increased by 200) are used to refer to the structural elements that are similar to those of the embodiment described above with respect to FIGS. 1-4. In the embodiment of FIGS. 9 and 10, a suture plate 370 has a circular portion 371 which is fitted over top wall 311 of the port device 300. The plate 370 has holes to accommodate the working ports 313A, 313B, 313C, and the insufflation port 314. The plate 370 also includes suture ears 326 which extend outwardly from the circular portion 371 and are connected to the circular portion 371 by a neck portion 372. The suture ears 326, necks 372, and circular portion 371 define suture grooves 327 which receive sutures for suturing the device 300 to tissue adjacent the entrance site. The suture plate 370 can be made substantially rigid when formed from a metal, polyoxymethylene such as Delrin, polycarbonate, polyurethane, poly(acrylonitrile-butadiene-styrene) which is commonly referred to as ABS, etc. Suture plate 370 can be adhered to surface 311 or held in place by mechanical locking means (not shown). When substantially rigid, the suture plate 370 will not bend or stretch much when held down with sutures. Alternatively, the suture plate 370 can be made from a more flexible when formed from a more flexible elastomeric material.

The port device 300 of FIG. 9 includes a reinforcement belt 380 placed in the upper section of the flexible tapered wall 342 so as to reinforce the wall 342 to maintain it round when inserted into the umbilicus. The length of the reinforcement belt 380 can be 5% to 33% of the axial length of the tapered wall 342. The thickness of the belt 380 is preferably between 0.5 mm and 1.5 mm. The belt 380 can be insert-molded in place or placed in the taper after completion of the device 300. It can also be appreciated that the thickness of the tapered frustoconical wall of any of the embodiments can be made thicker in the proximal area to accomplish the same reinforcement purpose. Ribs, both circumferential and longitudinal can be incorporated to function similarly.

FIGS. 11-17 show yet another embodiment of a port device 400. In the alternate embodiment of FIGS. 11-17, like numerals (increased by 300) are used to refer to the structural elements that are similar to those of the embodiment described above with respect to FIGS. 1-4. In this embodiment, the working ports 413 of port 400 have the same inner diameter (for example, 7 mm in diameter for smaller 5 mm diameter instruments such as scissors and graspers). Each of the working ports 413 is shown molded with a membrane 417 which can be slit to form a slit valve (e.g., an X or Y slit) or may be left as a blank and punctured by instrumentation at the time of use. Alternatively, each port may be molded with a tricuspid or duck-bill valve, or the O-shaped seal having an open circular hole in its center as shown in the first embodiment. As another alternative, each port may be fitted with a valve (not shown) to prevent pressure loss (desufflation) when an instrument is removed from the port.

Figure 16:
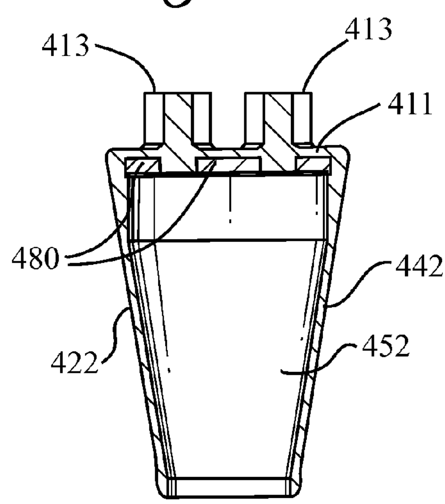
FIG. 16 is a two-dimensional cross-sectional view of the device of FIG. 11 along line B-B shown in FIG. 13.
Figure 12:
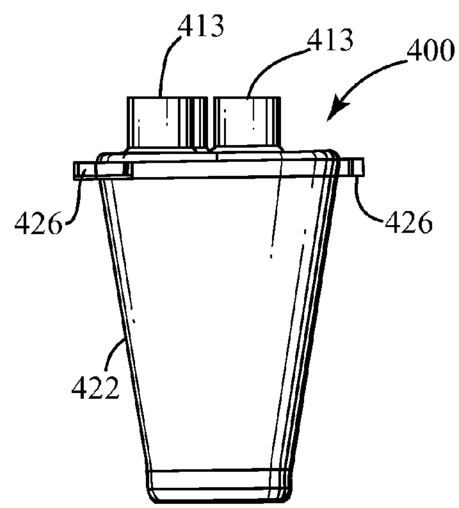
FIG. 12 is a side view of the device of FIG. 11.
Figure 14:
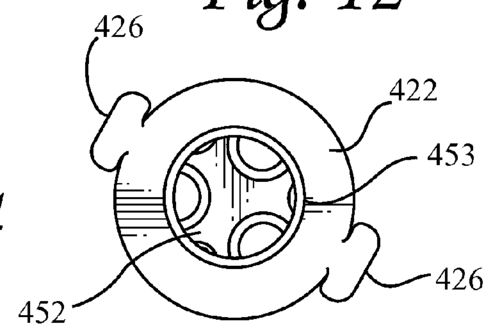
FIG. 14 is a bottom view of the device of FIG. 11.
Figure 15:
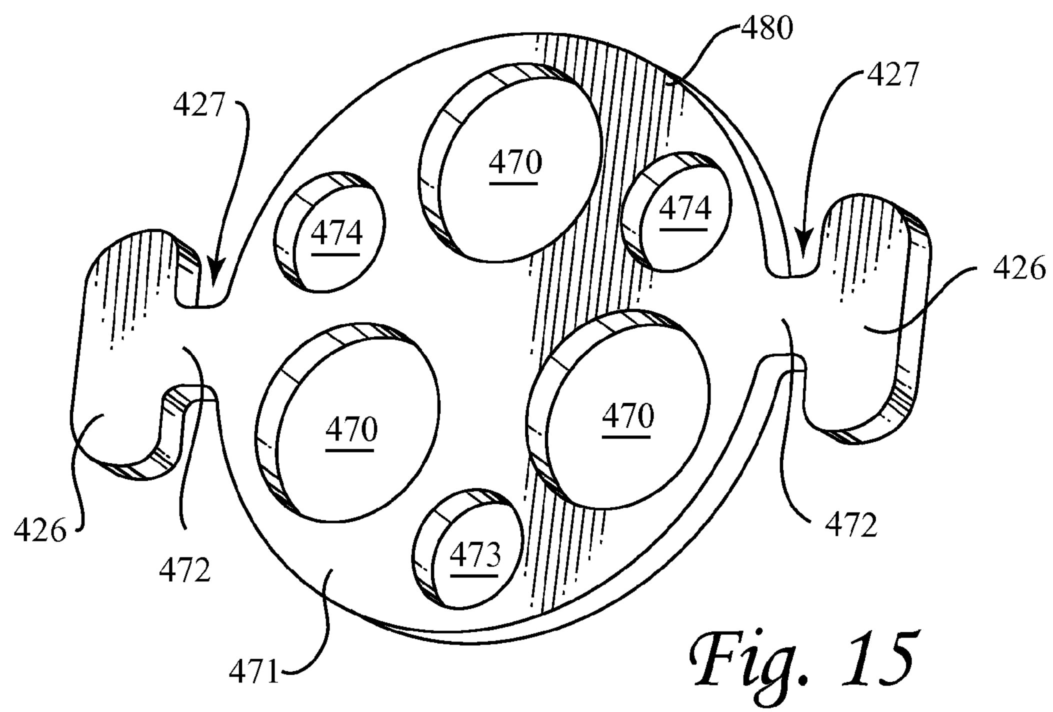
FIG. 15 is a perspective view of a plate molded into the device of FIG. 11.
Figure 17:
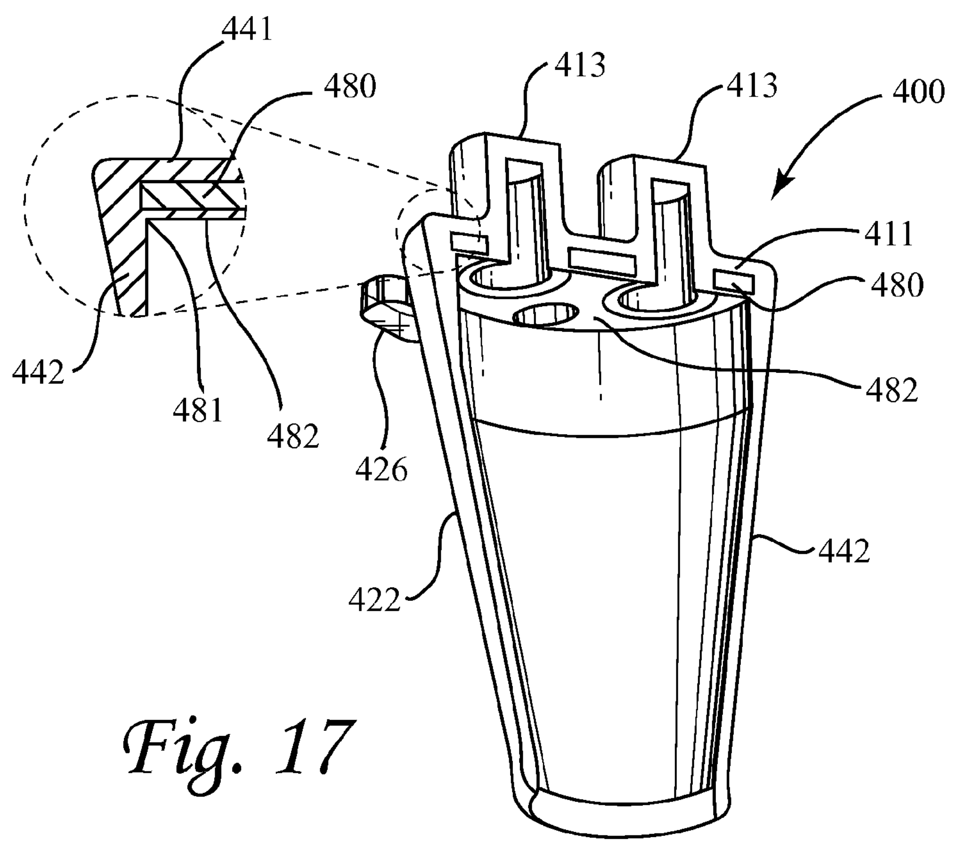
FIG. 17 is a three-dimensional cross-sectional view of the device of FIG. 11 along line C-C shown in FIG. 13.

The port 400 also preferably includes a reinforcement plate 480 (FIG. 15) formed as part of the top wall 411 of the frustoconical body 422 as best shown in FIGS. 16 and 17. The reinforcement plate 480 reinforces the tapered wall 442 of the body 422 to maintain it round when inserted into the umbilicus. In the preferred embodiment, the plate 480 is realized of a moldable or thermoformable polymeric material such as polycarbonate, stiff polyurethanes, metal, polymethylmethacrylate (Plexiglas®), polyacetal (Delrin®) or other suitable material. The plate 480 is preferably insert molded in place or otherwise placed in position adjacent the top wall 411 of the body 422 of the device 400. When insert molded, the material of the plate 480 is required to withstand the heat of the injection molding of the frustoconical body 422. The reinforcement plate 480 includes a first set of through-holes 470 that are aligned to corresponding ports 413 and sized to accommodate the tool(s) inserted through the respective corresponding port 413 and through-hole 470. In the preferred embodiment, the through-holes 470 are oversized relative to the diameter of the corresponding port 413, and during insert molding, the material that forms the top wall 411 and ports 413 form a central opening inside the oversized through-hole 470. This central opening matches (and is aligned to) the inside diameter of the corresponding port molded thereabove. Also note that the plate 480 is preferably held in place under and adjacent to the top wall 411 of the body 422 by a ledge 481 formed in the interior surface of the tapered sidewall 442 as shown in FIG. 17. Moreover, the material that is molded to form the top wall 411, sidewall 422 and ports 413 of the device 400 may be allowed to encapsulate the plate 480 by a thin layer 482 as shown in FIG. 17. The reinforcement plate 480 operates a pivot point about which to pivot the respective tool passing therethrough. The reinforcement plate 480 also preferably includes a through-hole 473 aligned with the insufflation port 414 to allow for gas to pass between the insufflation port 414 and the interior cavity 452 of the body 422. The plate 480 also preferably includes a second set of through-holes 474 that allows for inflow of material therein during insert molding to join the plate 480 to the top wall 411 of the body 422. The thickness of the plate 480 is preferably between 0.05 in and 0.25 in, and most preferably approximately 125 in. ±20%.

The plate 480 also has a plurality of suture ears 426 (for example, two shown) which extend outwardly from the circular portion 471 and are connected to the circular portion 471 by a neck portion 472. The suture ears 426, necks 472, and circular portion 471 define suture grooves 427 (FIG. 15) which receive sutures. The suture ears 426 will not bend or stretch much when held down with sutures. The suture ears 426 extend radially outward beyond the periphery of the top wall 411 of the body 422 such that suture grooves 427 are disposed about the periphery of the top wall 411 of the body. The suture grooves 427 are adapted to grab or otherwise hold sutures inserted therein for fixation of the port 400 during use. In the illustrative embodiment shown in FIG. 15, the plate 480 has two suture ears 426 that are disposed diametrically apart. During use, the ears 426 are sutured to the incision and the ears 426 joined through the plate 480 act as a rigid axle that allows the port 480 to rock back and forth in the incision. This freedom of movement allows for greater control of the surgical tools.

The ports 100, 200, 300 and 400 of the embodiments as described herein have sidewalls which are frustoconical in shape. The sidewall (142, 242, 342, 442) of the respective port device as described herein preferably has a major outside diameter (measured at or near the perimeter of the top wall) in a range between 30-40 mm (most preferably 35 mm) and tapers in diameter to a minor outside diameter (measured at or near the distal opening 153, 253, 353, 453) in a range between 10-20 mm (most preferably 15 to 18 mm). The length of the sidewall (142, 242, 342, 442) as measured from the center axis of the top wall to the center of the distal opening preferably has a range from 20 to 35 mm; however, it can be cut to length in situ by the surgeon, preferably at grooves 159, 259. Such configurations provide a slope angle a of the sidewall (142, 242, 342, 442) in a range between 10° and 20°, preferably 15°-17° (a 16° angle being shown in FIG. 8). The wall thickness of the sidewall is sufficiently thick so that the wall will not readily buckle when placed in the umbilicus and when dilating the incision, yet sufficiently flexible to allow distortion when an instrument is forced against it. The sidewall (142, 242, 342, 442) is not meant to hug the instrumentation nor provide a seal against the instrumentation. Typical wall thicknesses are 0.5 mm to 3 mm; preferably, 1 mm to 2 mm. If desired, the sidewall (142, 242, 342, 442) may be tapered in wall thickness with the sidewall adjacent the top wall having a relatively larger thickness (e.g., 2 mm), and the sidewall near the distal opening being relatively thinner (e.g., 1 mm in thickness). Also, as shown in FIGS. 5, 8 and 10, if desired, the sidewall at the distal opening can taper sharply (shown as 222*a*) down to a minimal thickness. With the frustoconical sidewall being tapered in thickness, the portion of the sidewall which is subject to the most compressive force in the umbilicus will not easily buckle, and at the same time, as suggested by FIG. 18, the distal portion of the sidewall will be more flexible to permit a wider freedom of movement to the laparoscopic tools 264, 265 extending through the working ports of the port device.

The port device 100, 200, 300, 400 as described herein can be made as a single injection molded piece in an injection or compression molding machine. As such, it is relatively inexpensive to make and is therefore disposable.

The ports of the present invention functions as follows: First, an incision 10-15 mm wide is made in the umbilicus using the Hassan procedure. The narrow end of the tapered sidewall (142, 242, 342, 442) of the device is inserted into the incision and forced downward such that the incision is stretched sufficiently by the tapered sidewall to engage the tissue and provide a seal between the tissue and the tapered sidewall. The working ports, central cavity and opening opposite the top wall of the port provide a passageway for three laparoscopic instruments (which have approximately 5 mm or 10 mm cannulas) to be inserted into the abdominal cavity. In addition, the insufflation port provides a means by which the abdominal cavity may be inflated. The port device may be sutured in place if desired. An operation may then be conducted through the working ports. Upon conclusion of the operation, and if for example the operation involved removal of an organ (e.g., infected gall bladder), the organ can be pulled into the hollow frustoconical structure, the sutures removed from the ears and the entire port with the organ housed in the hollow structure removed. In this manner the organ does not touch the fascia or epidermis, which may otherwise result in infection of the incision site. Once the port is removed, the sutures can be further used to close the incision in any manner known in the art. Alternatively, the port may be removed from the incision, and the incision closed in any manner known in the art.

Figure 18:
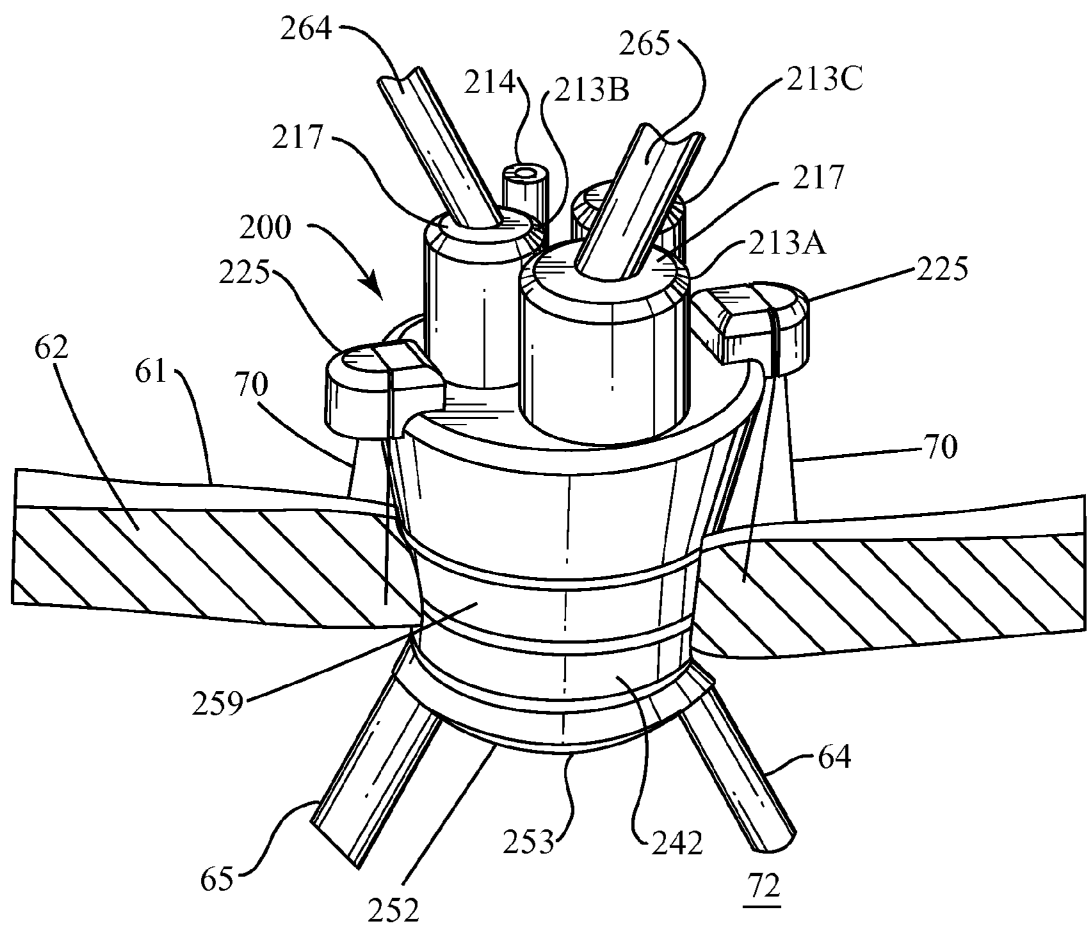
FIG. 18 is a perspective view of the device of FIG. 5 shown sutured in place in an abdomen with tools extending through two of the ports.

FIG. 18 shows the flexible disposable port 200 of FIGS. 5-8 placed in an incision in the umbilicus, comprised of epidermis 61 and facia 62. The tapered (frustoconical) sidewall 242 of the port 200 both seals the incision in the umbilicus such that gas used to inflate the abdominal cavity does not leak between the umbilicus and taper, and dilates the opening to allow a larger working area. If the surgeon so desires, the tapered sidewall 242 can be cut with a scissors or blade at the circumferential rings 259 (FIG. 7) to shorten the tapered sidewall 242 and to provide a wider area of unrestricted movement of the instruments. Instruments 264 and 265 are pierced through membranes 217 that cover the entrance to the working ports 213B and 213A, respectively. The instruments 264, 265 pass through the working ports 213B, 213A and transcend the central cavity 252 defined by the tapered sidewall 242 and exit through the distal opening 253 into the abdominal space 72. Note that the flexible tapered sidewall 242 is deformable about its distal portion to enable maneuvering of the instrumentation 264 and 265 over a broader area. The port 200 is held firmly in place by sutures 70 snagged into the slots 229 (FIG. 6) of the suture retention means 225 and sewn into the adjacent tissue. Note that relatively large organs can be removed from the abdominal space 72 when the port 200 is removed from the umbilicus entrance site following completion of surgery. For example, a 30 mm diameter gall bladder may be removed from the umbilicus incision. It should be appreciated that surgery through the umbilicus is less painful than surgery through other parts of the abdomen as there are fewer pain receptors as well as less muscle to cut through. Accordingly it also heals faster with less chance of complication.

Other features can be added to the flexible surgical port device. For example, the flexible surgical port device can include a built-in light on the inside of the device to illuminate the cavity. Luer fittings can be added to the ports; especially the insufflation port. In addition, the flexible nature of each individual working port allows each working port to be clamped with a hemostat to prevent deflation of the abdominal cavity if necessary. If required, each working port can be fitted with a tethered stopper to enable plugging the working port when not in use. Further the working ports can be fabricated as bellows to facilitate movement of the instruments and port stems. The device can also have attachment means on the port entrances to allow attachment of caps that contain valves or blanks. Still further, a section of material 441 (FIG. 17) in the center of the plate between the working channels 413, can be removed to expose the plate 480. If a clear material, such as polycarbonate is used to form the plate 480, then removing the material enables a clear window to be formed through the top of the port to enable direct visualization of the abdominal cavity.

The flexible disposable port devices described herein can be made from any flexible elastomeric material, for example, silicone rubber, polyurethane, polyolefin (such as SIBS, SEBS, butyl rubber, etc.), polyvinylchloride, natural rubber, and the like. SIBS is a block copolymer of styrene-block-isobutylene-block-styrene. SEBS is a block copolymer of styrene-block-ethylene-butylene-block-styrene. The flexible elastomeric material preferably has a Durometer less than Shore 80 A and greater than Shore 20 A, and most preferably in a range between Shore 60 A and Shore 30 A. The flexible elastomeric material also preferably has a modulus of elasticity at 100% elongation (referred to herein as "Modulus@100%" greater than 0.5 Mpa and less than 1.5 MPa such that port device seals around umbilical entrance site and the laparoscopic tools inserted therethrough as well as provide for innocuous operation of the tool when it touches the distal end of the tapered sidewall (FIG. 18). If the Modulus@100% is less than 0.5 Mpa, the tapered sidewall would buckle in the umbilical entrance site. If the Modulus@100% is greater than 1.5 Mpa, the ports of the device will not easily and quickly seal around the tool(s) inserted therethrough. The flexible elastomeric material also preferably has a tensile strength of greater than 10 MPa, a percent of elongation at break greater than 600%, and a tear strength greater than 20 KNm so as not to tear after prolonged use in the body.

In the embodiments of FIGS. 1-4 and FIGS. 5-9, it is preferable that the entire device be made from one polymer and as one piece, either by injection molding or compression molding. A filler (such as titanium dioxide) can be added to the elastomeric material as needed to dictate the color and transparency of the device.

In the preferred embodiment, the flexible disposable port devices described herein are made from SIBS. SIBS is realized from a triblock of polyisobutylene and polystyrene (a block copolymer of poly(styrene-block-isobutylene-block-styrene)). Polyisobutylene (PIB) is a soft elastomeric material with a Shore hardness of approximately 10 A to 30 A. When copolymerized with polystyrene, it can be made at hardnesses ranging up that of polystyrene having a Shore hardness of 100 D. Thus, depending on the relative amounts of polystyrene and polyisobutylene, the SIBS material can have a range of hardnesses from as soft as Shore 10 A to as hard as Shore 100 D. In this manner, the SIBS material can be adapted to have elastomeric and hardness qualities desirable for the flexible port devices as described herein. Details of the SIBS material is set forth in U.S. Pat. Nos. 5,741,331; 6,102,939; 6,197,240; 6,545,097, which are hereby incorporated by reference in their entireties. The SIBS material may be polymerized in a controlled manner using carbocationic polymerization techniques such as those described in U.S. Pat. Nos. 4,276,394; 4,316,973; 4,342,849; 4,910,321; 4,929,683; 4,946,899; 5,066,730; 5,122,572; and Re 34,640, each herein incorporated by reference in their entireties. The amount of styrene in the copolymer material is preferably between 10 mole % and 25 mole % and most preferably between 17 mole % and 22 mole %. The polystyrene and polyisobutylene copolymer materials are preferably copolymerized in solvents.

Alternative polymeric materials can be used for the device. Such alternative polymeric materials preferably include polyisobutylene-based material capped with a glassy segment. The glassy segment provides a hardener component for the elastomeric polyisobutylene. The glassy segment can be a vinyl aromatic polymer (such as styrene, $\alpha$-methylstyrene, or a mixture thereof), or a methacrylate polymer (such as methylmethacrylate, ethylmethacrylate, hydroxymethalcrylate, or a mixture thereof). Such materials preferably have a general block structure with a central elastomeric polyolefinic block and thermoplastic end blocks. Even more preferably, such materials have a general structure:

BAB or ABA (linear triblock), $B(AB)_n$ or $a(BA)_n$ (linear alternating block), or $X\text{-}(AB)_n$ or $X\text{-}(BA)_n$ (includes diblock, triblock and other radial block copolymers), where A is an elastomeric polyolefinic block, B is a thermoplastic block, n is a positive whole number and X is a starting seed molecule.

Such materials may be star-shaped block copolymers (where n=3 or more) or multi-dendrite-shaped block copolymers. These materials collectively belong to the polymeric material referred to herein as SIBS.

Forming the port devices as described herein from SIBS is preferred because SIBS affords the advantages of superb biocompatibility and biostability characteristics, ease of injection molding, ease of insert molding (particularly for insert molding the reinforcement band or reinforcement plate as described herein), ease of solvent bonding (for example, bonding valves to the ports of the device), accurate control over the Durometer of the material over the required range of Durometer (e.g., between Shore 80 A and Shore 20 A), providing a Modulus@100% within the preferred range between 0.5 Mpa and 1.5 MPa, and providing tensile characteristics (tensile strength, percent of elongation at break, and tear strength) that minimizes tearing of the port device after prolonged use in the body.

Table 1 below illustrates the properties of three different grade SIBS as compared to other flexible elastomeric materials.

| Property | | Material | | | | | | |
|---|---|---|---|---|---|---|---|---|
| | | SIBS (073T) 20 mole % styrene, molecular weight of | SIBS (103T) 20 mole % styrene, molecular weight of | SIBS (102T) 8 mole % styrene, molecular weight of | | SEPS (styrene | SBS (styrene | SEBS (styrene |
| Property Name | Unit | ~70,000 Dalton | ~100,000 Dalton | ~100,000 Dalton | Silicone (4940) | ethylenepropylene styrene) | butadiene styrene) | ethylenebutylene styrene) |
| Hardness | Shore A | 45-47 | 46-50 | 25-30 | 40 | 80 | 70 | 77 |
| Modulus at 100% | MPa | 0.9 | 1.0 | 0.5-0.7 | 2 | 3.7 | 2.0 | 2.4 |
| Tensile Strength at break | MPa | 14 | 18 | 16 | 7.6 | 42 | 31 | 34 |
| % Elongation at break | % | 650 | 620 | 870 | 550 | 480 | 860 | 500 |
| Tear Strength | KN/m | 26 | 38 | 25 | 44 | 46 | 47 | 44 |

Figure 19:
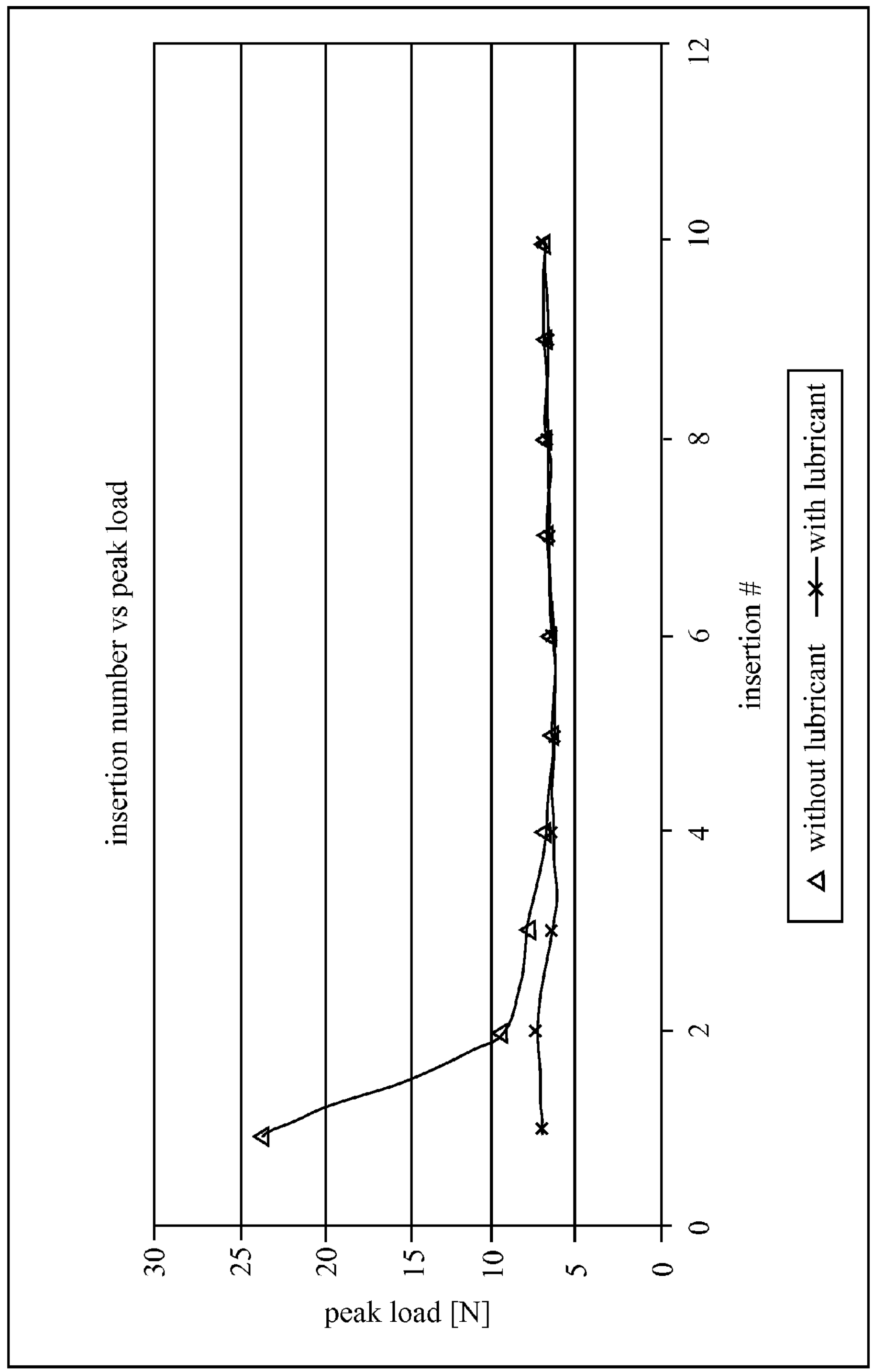
FIG. 19 is a graph comparing the sliding force required for a laparoscopic instrument through lubricated and non-lubricated SIBS valves.

According to one aspect of the invention, it is desirable to form the port devices as described herein from SIBS because SIBS does not require lubrication of the ports (or of the instruments extending through the ports) to enable better sliding of the instrumentation in the respective ports. More particularly, as shown in FIG. 19, upon initial tool insertion into SIBS ports without lubrication, a relatively large force is required, but thereafter the required insertion force of the non-lubricated SIBS port is similar to a lubricated port. By avoiding the need for such lubrication, the risk of infection stemming from such lubrication is avoided. This feature was unexpected and provides significant advantages. Moreover, it is contemplated that an instrument can be inserted into the non-lubricated SIBS port one or more times at the time of manufacture (or at the time of distribution or prior to use) such the surgeon does not experience the large initial insertion force of the non-lubricated SIBS port. Those well versed in the art will understand that the sliding forces of the instrument through the port are a function of the material, the lubricity and the design of the port. For example, if the port is a simple slit, the length of the slit will contribute to the overall force required to insert a tool. For example if the port is long, e.g., 0.25" long, the force required to insert a 5 mm diameter tool will be low, but the leakage rate of gas around the tool may be too high. Alternatively, if the slit is 0.125" long, the leakage rate will be zero but the tool will not slide as easily. With a slit length of 0.1875", the leakage rate is approximately zero with easy slidability. It is desirable during laparoscopic surgery that the flow rate of carbon dioxide be set at 15 L/min which provides a pressure in the abdominal cavity of approximately 12-15 mmHg. The port construction should be such that the pressure drop during a procedure should be less than 3 mmHg.

In yet other embodiments, the flexible elastomeric material from which the port devices as described herein are formed can contain fillers such as Teflon particles or oils to lubricate the ports to enable better sliding of the instrumentation in the respective ports. The device can also be made with slippery surfaces (hydrophilic or hydrophobic) to facilitate sliding of the instrument in the ports. Also, although sutures and suture snaggers, both rigid and flexible are shown to hold the port in place, a belt placed around the abdomen of the patient that contains the port device of the invention will accomplish the same. In addition, the tapered outer surface can be made sticky to decrease sliding, or a flange can be added to the proximal end with an adhesive on the inner surface to further aid in maintaining the port in place.

In accord with another aspect of the invention, the side wall could be stepped so that it is generally frustoconical (e.g., it has several frustoconical sections). The side wall could also be stepped or threaded with a helical interface to enable the sidewall to be screwed into the incision. In accord with a further aspect of the invention, the thickness of the frustoconical side wall could change in steps or gradually over the length of the port device. In accord with an additional aspect of the invention, rather than having ports extending outward from the top wall, no outwardly extending ports are provided, and the ports consist of holes in the top wall of the port device. Alternatively, the ports can extend a little inside the frustoconical outer wall. Finally, instead of three working ports and an optional insufflation port, a different number of working ports (e.g., four) can be provided. Those skilled in the art will understand that other modifications to this device can be made without deterring from the scope of this invention.

There have been described and illustrated herein several embodiments of a flexible elastomeric surgical port device and surgical method of using same. While particular embodiments of the invention have been described, it is not intended that the invention be limited thereto, as it is intended that the invention be as broad in scope as the art will allow and that the specification be read likewise. Thus, while particular flexible elastomeric materials have been disclosed, it will be appreciated that other elastomeric materials can be used as well. In addition, while particular port and valve configurations have been disclosed, it will be understood that other suitable port and valve configurations can be used. Moreover, while particular configurations have been disclosed in reference to integrated reinforcement of the port body, it will be appreciated that other configurations could be used as well. It will therefore be appreciated by those skilled in the art that yet other modifications could be made to the provided invention without deviating from its spirit and scope as claimed.

What is claimed is:

1. A surgical apparatus for introduction of laparoscopic instruments into an anatomical cavity through tissue at an entry site, said apparatus comprising:

a one-piece molded polymeric body with a frustoconical-shaped wall with an exterior sealing surface for sealable contact with the tissue at the entrance site, the body defining an interior cavity, an open bottom, and a substantially closed top wall with openings from which a plurality of ports extend upward therefrom, the plurality of ports for receiving the laparoscopic instruments for introduction through the interior cavity and open bottom of the body into the anatomical cavity;

wherein the frustoconical-shaped wall tapers continuously from a large diameter adjacent the substantially closed top wall to a smaller diameter that defines the open bottom of the body; and wherein the top wall of the body has a reinforcement plate formed of a material different and relatively stiff with respect to the polymeric material of the body, the reinforcement plate including thru-holes that accommodate the plurality of ports, and the reinforcement plate configured to operate as a pivot point about which to pivot a respective laparoscopic instrument that passes through a corresponding thru-hole of the reinforcement plate.

2. A surgical apparatus according to claim 1, further comprising:

suture retention means for suturing the body to tissue adjacent the entry site.

3. A surgical apparatus according to claim 2, wherein:

the suture retention means are disposed within the radial periphery of the top wall of the body.

4. A surgical apparatus according to claim 2, wherein:

the suture retention means is integrally formed on a top surface of the top wall of the body about the perimeter of the top wall of the body.

5. A surgical apparatus according to claim 2, wherein:

the suture retention means is integrally formed as part of the reinforcement plate and is disposed about the perimeter of the top wall of the body.

6. A surgical apparatus according to claim 2, wherein:

the suture retention means is integrally formed as part of the reinforcement plate and extends radially outward beyond the frustoconical-shaped wall of the body.

7. A surgical apparatus according to claim 1, wherein:

the reinforcement plate is configured to reinforce the body such that the frustoconical-shaped wall maintains its shape when inserted through tissue at the entry site.

8. A surgical apparatus according to claim 1, wherein:

the reinforcement plate includes integrally formed suture retention means that extend radially outward beyond the frustoconical-shaped wall of the body, the suture retention means for suturing the body to tissue adjacent the entry site.

9. A surgical apparatus according to claim 1, wherein:

the plurality of thru-holes correspond to the ports of the body, and each thru-hole is sized to match the corresponding port.

10. A surgical apparatus according to claim 9, wherein:

the reinforcement plate has a sidewall, a major top surface and a major bottom surface, and the reinforcement plate is integrally formed with the top wall of the body by insert molding such that the material of the top wall encapsulates the side wall and the major top and bottom surfaces of the reinforcement plate.

11. A surgical apparatus according to claim 1, wherein:

the reinforcement plate includes at least one thru-hole that allows for inflow of material during insert molding of the body.

12. A surgical apparatus according to claim 1, wherein:

the material of the reinforcement plate is selected from the group including a metal, polyoxymethylene, polycarbonate, polyurethane, and poly(acrylonitrile-butadiene-styrene).

13. A surgical apparatus according to claim 1, wherein:

the material of the body comprises poly(styrene-block-isobutylene-block-styrene) having a Hardness of between 30A and 60A, a tensile strength of greater than 10MPa, a tear strength of greater than 20 KNm, and an elongation percentage at break of greater than 600%.

14. A surgical apparatus according to claim 1, wherein:

the frustoconical-shaped wall of the body has spaced circumferential grooves for assisting cutting or trimming to a desired length.

15. A surgical apparatus according to claim 1, wherein:

the interior cavity of the body is adapted to receive an organ for removal from the anatomical cavity without contacting the tissue at the entry site.

16. A surgical apparatus for introduction of laparoscopic instruments into an anatomical cavity through tissue at an entry site, said apparatus comprising:

a polymeric body with a frustoconical-shaped wall with an exterior sealing surface for sealable contact with the tissue at the entrance site, the body defining an interior cavity, an open bottom, and a substantially closed top wall with openings from which a plurality of ports extend upward therefrom, the plurality of ports for receiving the laparoscopic instruments for introduction through the interior cavity and open bottom of the body into the anatomical cavity;

wherein the frustoconical-shaped wall tapers continuously from a large diameter adjacent the substantially closed top wall to a smaller diameter that defines the open bottom of the body;

wherein the top wall a reinforcement plate formed of a material different and relatively stiff with respect to the polymeric material of the body, the reinforcement plate including thru-holes that accommodate the plurality of ports, and the reinforcement plate configured to operate as a pivot point about which to pivot a respective laparoscopic instrument that passes through a corresponding thru-hole of the reinforcement plate; and wherein the polymeric material of the body comprises poly(styrene-block-isobutylene-block-styrene) having a Hardness of between 30A and 60A, a tensile strength of greater than 10MPa, a tear strength of greater than 20 KNm, and an elongation percentage at break of greater than 600%.

17. A surgical apparatus according to claim 16, wherein:

the body is unitary one-piece molded structure.

18. A surgical apparatus for introduction of laparoscopic instruments into an anatomical cavity through tissue at an entry site, said apparatus comprising:

a one-piece molded polymeric body with a frustoconical-shaped wall with an exterior sealing surface for sealable contact with the tissue at the entrance site, the body defining an interior cavity, an open bottom, and a substantially closed top wall with openings from which a plurality of ports extend upward therefrom, the plurality of ports for receiving the laparoscopic instruments for introduction through the interior cavity and open bottom of the body into the anatomical cavity;

wherein the frustoconical-shaped wall tapers continuously from a large diameter adjacent the substantially closed top wall to a smaller diameter that defines the open bottom of the body, wherein the top wall of the body has a reinforcement plate formed of a material different and relatively stiff with respect to the polymeric material of the body, the reinforcement plate having a sidewall, a major top surface and a major bottom surface, the reinforcement plate integrally formed with the top wall of the body by insert molding such that the material of the top wall encapsulates the side wall and the major top and bottom surfaces of the reinforcement plate, the reinforcement plate further including thru-holes that accommodate the plurality of ports, and the reinforcement plate configured to operate as a pivot point about which to pivot a respective laparoscopic instrument that passes through a corresponding thru-hole of the reinforcement plate.

* * * * *